(12) United States Patent
Nakayama et al.

(10) Patent No.: US 9,814,232 B2
(45) Date of Patent: Nov. 14, 2017

(54) INSECT CONTROL SHEET

(71) Applicants: NISSHA PRINTING CO., LTD., Kyoto-shi, Kyoto (JP); NATIONAL UNIVERSITY CORPORATION KYOTO INSTITUTE OF TECHNOLOGY, Kyoto-shi, Kyoto (JP)

(72) Inventors: Tetsuya Nakayama, Kyoto (JP); Yasuisa Takinishi, Kyoto (JP); Yoshihide Inako, Kyoto (JP); Hajime Mori, Kyoto (JP); Tomoko Hirano, Kyoto (JP); Yoshihiro Harada, Kyoto (JP)

(73) Assignees: NISSHA PRINTING CO., LTD., Kyoto-shi, Kyoto (JP); NATIONAL UNIVERSITY CORPORATION KYOTO INSTITUTE OF TECHNOLOCY, Kyoto-shi, Kyoto (JP)

( * ) Notice: Subject to any disclaimer, the term of this patent is extended or adjusted under 35 U.S.C. 154(b) by 0 days.

(21) Appl. No.: 15/026,855

(22) PCT Filed: Feb. 12, 2015

(86) PCT No.: PCT/JP2015/053784
§ 371 (c)(1),
(2) Date: Apr. 1, 2016

(87) PCT Pub. No.: WO2015/125684
PCT Pub. Date: Aug. 27, 2015

(65) Prior Publication Data
US 2016/0249609 A1 Sep. 1, 2016

(30) Foreign Application Priority Data

Feb. 18, 2014 (JP) ................................ 2014-028592

(51) Int. Cl.
*A01N 25/34* (2006.01)
*A01M 1/20* (2006.01)
*A01N 63/02* (2006.01)

(52) U.S. Cl.
CPC .......... *A01N 25/34* (2013.01); *A01M 1/2016* (2013.01); *A01M 1/2055* (2013.01); *A01N 63/02* (2013.01)

(58) Field of Classification Search
CPC .... A01M 1/2016; A01M 1/20; A01M 1/2055; A01M 1/02; A01N 25/34; A01N 25/00; A01N 63/02; A01N 63/00
See application file for complete search history.

(56) References Cited

U.S. PATENT DOCUMENTS 4,631,857 A * 12/1986 Kase .................. A01M 1/20
                                                  43/131
4,927,635 A * 5/1990 Loschiavo ............. A01M 1/02
                                                  424/405
(Continued)

FOREIGN PATENT DOCUMENTS

JP     H06-197676 A     7/1994

OTHER PUBLICATIONS

PCT/IB/326, "Notification Concerning Transmittal of International Preliminary Report on Patentability for International Application No. PCT/JP2015/053784," dated Sep. 1, 2016.
(Continued)

*Primary Examiner* — Kathleen I Alker
(74) *Attorney, Agent, or Firm* — Manabu Kanesaka

(57) ABSTRACT

An insect control sheet containing a Cry polyhedron prepared by fixing an insecticidal protein (a Cry toxin) produced by *Bacillus thuringiensis* to a polyhedron of polyhedrin protein is provided. The insect control sheet contains the Cry polyhedron and is used by floating on water. The (Continued)

Figure 1:
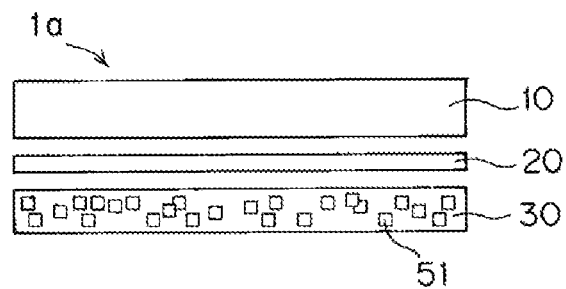
Figure 2:
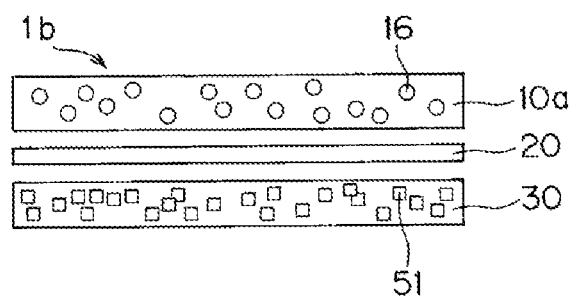
Figure 3:
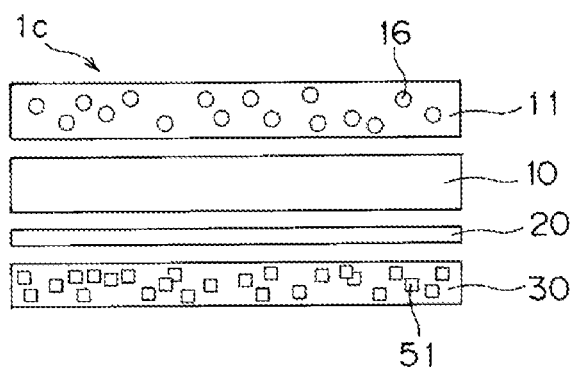
Figure 4:
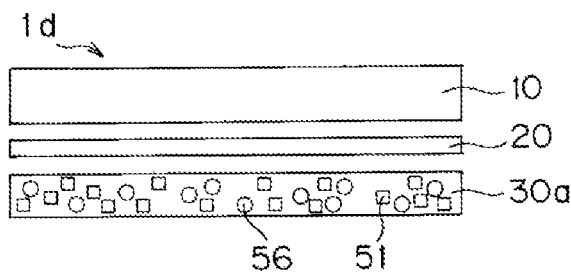

insect control sheet is floatable on water, and includes a pure matrix layer 20 and a toxin-containing matrix layer 30 containing the Cry polyhedron 51 which are layered on the underside of a sheet-shaped first sheet substrate 10. The pure matrix layer 20 is composed of a degradable or water-soluble second material and the toxin-containing matrix layer 30 is composed of a degradable or water-soluble third material and the Cry polyhedron. The toxin-containing matrix layer sustainably releases the Cry polyhedron to the water on which the insect control sheet is floated.

11 Claims, 4 Drawing Sheets

(56) References Cited

U.S. PATENT DOCUMENTS

| | | | | |
|---|---|---|---|---|
| 5,046,280 | A * | 9/1991 | Foster | A01M 1/02 43/131 |
| 6,338,846 | B1 * | 1/2002 | Kang | A01N 63/00 424/93.2 |
| 6,662,491 | B2 * | 12/2003 | Flinn | A01M 1/2055 424/405 |
| 6,718,689 | B1 * | 4/2004 | Kolibas | A01M 1/2005 43/131 |
| 6,898,898 | B1 * | 5/2005 | Cohen | A01M 1/20 43/124 |
| 7,605,304 | B2 * | 10/2009 | Abad | C07K 14/325 536/23.71 |
| 8,269,069 | B1 * | 9/2012 | Narva | C07K 14/325 514/4.5 |
| 2007/0031463 | A1 * | 2/2007 | Fotinos | A01M 1/2055 424/405 |
| 2010/0029725 | A1 * | 2/2010 | Cosgrove | A01N 63/02 514/359 |
| 2010/0158965 | A1 * | 6/2010 | Beitzel | A01N 25/34 424/405 |
| 2015/0072862 | A1 * | 3/2015 | Dujardin | B29C 47/92 504/215 |

OTHER PUBLICATIONS

PCT/IB/373, "International Preliminary Report on Patentability for International Application No. PCT/JP2015/053784," dated Aug. 23, 2016.
PCT/ISA/237, "Written Opinion of the International Searching Authority for International Application No. PCT/JP2015/053784," dated May 19, 2015.
PCT/IB/338, "Notification of Transmittal of Translation of the International Preliminary Report on Patentability for International Application No. PCT/JP2015/053784," dated Sep. 1, 2016.
PCT, "International Search Report for International Application No. PCT/JP2015/125684".
Shinichiro Asano "Possibility of insect pathogenic microbe as hygine insect pest control materials", Journal of Pesticide Science.
Michio Himeno "Improvement and mechanism of action of microbial pesticides", Microbes and Environments, 1999, vol. 14, No. 4,, 245 to 252.
Biomaterials 30 (2009) 4297-4308, Structure-based targeting of bioactive proteins into cypovirus polyhedra and appliaiton to immobilized cytokines for mammalian cell culture, Hiroshi Ijiri et al.
Using the bio-insecticide Bacillus thuringiensis israelensis in Mosquito control, www.intechopen.com.
Binding of Cyt1Aa and Cry11Aa Toxins of Bacillus thuringiensis Serover israelensis to Brush Border Membrane Vesicles of Tipula paludosa (Diptera: nematocera_and Subsequent pore formation, Journals.ASM.org. January 29, 20114.
Yoshihiro Harada, Eiji Kotani; Shinichiro Asano & Hajime Mori; "Fixation of the δ-endotoxins of Bacillus thuringiensis to polyhedra and application thereof", A6 in "The collection of the lectures in Kansai area", distributed at "The Academic Lectures for the Study and Use of Insect Functions", The Joint Meeting of the Japanese Society of Sericultural Science, Nov. 10, 2012.

* cited by examiner

INSECT CONTROL SHEET

RELATED APPLICATIONS

The present application is National Phase of International Application No. PCT/JP2015/053784 filed Feb. 12, 2015, and claims priority from Japanese Application No. 2014-028592, filed Feb. 18, 2014, the disclosure of which is hereby incorporated by reference herein in its entirety.

TECHNICAL FIELD

The present invention relates to an insect control sheet used by floating on water.

BACKGROUND ART

The insecticidal protein produced by *Bacillus thuringiensis* (hereinafter referred to as a "Cry toxin") exerts an insecticidal activity against certain species of insects. The Cry toxin produced by *Bacillus thuringiensis* serovar israelensis is known to be toxic to mosquito larvae.

The inventors fixed the Cry toxin to a polyhedron of polyhedrin protein, which is a protein microcrystal produced by Bombyxmori cypovirus (BmCPV). The Cry toxin fixed to the polyhedron is hereinafter referred to as a "Cry polyhedron". A tag for fixing the Cry toxin to the polyhedron of polyhedrin protein was added to the N-terminal of the Cry toxin. Then the tagged Cry toxin was fixed to the polyhedron of polyhedrin protein.

The inventors reported that
(1) the Cry polyhedron exerted an insecticidal activity against mosquito larvae, and
(2) mosquito larvae which ingested the Cry polyhedron died (refer to the non-patent literature 1).

On the other hand, a method for making mosquito larvae easily ingest the Cry polyhedron at their habitat in natural environment was not found at that time.

CITATION LIST

Non-Patent Literature

NPL 1: HARADA Yoshihiro, KOTANI Eiji, ASANO Shinichiro, & MORI Hajime, "Fixation of the δ-endotoxins of *Bacillus thuringiensis* to polyhedra and application thereof", A6 in "The collection of the lectures in Kansai area", distributed at "the Academic Lectures for the Study and Use of Insect Functions", the Joint Meeting of the Japanese Society of Sericultural Science, Nov. 10, 2012

SUMMARY OF INVENTION

Technical Problem

The problems to be solved by the invention is fabricating insect control sheets and articles containing the Cry polyhedron as the active ingredient, and harmful insects easily ingesting the Cry polyhedron, and also finding a means of the same.

Other problems to be solved by the present invention are apparently explained in the following description of the present invention.

Solution to Problem

The means for solving the problems will be described below. The signs used in the description correspond to the signs in the embodiments of the present invention for the convenience of understanding, and the present invention is not restricted within the scope of the embodiments. The numbers used as the signs may collectively represent the parts, and alphabetical letters are sometimes added to the numbers to represent each of the parts in the working examples mentioned below.

An insect control sheet according to an embodiment of the present invention comprises an insecticidal protein produced by *Bacillus thuringiensis* (hereinafter referred to as a "Cry toxin") and fixed to a polyhedron of polyhedrin protein (the Cry toxin fixed to the polyhedron hereinafter referred to as a "Cry polyhedron"), and is used by floating on water surface. The insect control sheet comprises a sheet-shaped first sheet substrate (10), a pure matrix layer (20) layered on the underside of the first sheet substrate (10), and a toxin-containing matrix layer (30) containing the Cry polyhedron (51) and layered on the underside of the pure matrix layer, and the insect control sheet floats on water. Also, the insect control sheet comprises, the pure matrix layer is composed of a degradable or water-soluble second material, the toxin-containing matrix layer is composed of a degradable or water-soluble third material and the Cry polyhedron; and the toxin-containing matrix layer sustainably releases the Cry polyhedron to the water on which the insect control sheet is floated.

Harmful insects include those killed by the Cry toxin, for example, insects falling into Diptera, Coleoptera and Lepidoptera.

Mosquito larvae (called "bofura" or "bofuri" in Japanese) falling into the category of harmful insects usually float in water between water surface and several centimeters below water surface. Mosquito larvae regularly go up to water surface to breathe and feed in water. The Cry polyhedron has a specific gravity of 1.27.

A suspension of the Cry polyhedron may come to one's mind as a Cry polyhedron-containing insecticide to kill mosquito larvae. However, the Cry polyhedron soon settles out after addition of the suspension to water without remaining within several centimeters below water surface, and fails to provide mosquito larvae the chance of ingestion. Thus the suspension of the Cry polyhedron cannot effectively exert its insecticidal activity against mosquito larvae.

The insect control sheet of the present invention
(1) floats on water surface, and
(2) comprises, in addition to other elements, the toxin-containing matrix layer composed of the degradable or water-soluble third material and the Cry polyhedron. The toxin-containing matrix layer sustainably releases the Cry polyhedron to the water on which the insect control sheet is floated. Consequently the Cry polyhedron is constantly supplied to the habitat, namely feeding place, of mosquito larvae, and exerts its insecticidal activity against mosquito larvae which ingest the Cry polyhedron.

The insect control sheet according to a preferred embodiment of the present invention may include the second material composed of the same ingredients as that of the third material. The third material may be composed of specific ingredients.

The specific ingredients have low human health risks to make the insect control sheet preferable to be used in a water tank for daily life water including drinking water.

Another insect control sheet according to a preferred embodiment of the present invention includes the first sheet substrate composed of a degradable first material. The toxin-containing matrix layer and the pure matrix layer may degrade or dissolve in water in a shorter time than that required for the decomposition or dissolution of the first sheet substrate.

The insect control sheet of the preferred embodiment is composed of the elements all of which degrade or dissolve in water. The sheet substrate retains its form throughout the period in which the toxin-containing matrix layer releases the Cry polyhedron, and thus enables the sustainable release of the Cry polyhedron from the degradable insect control sheet.

The insect control sheet of the preferred embodiment has the advantage that the sheet leaves no residue after use.

An insect control sheet according to another preferred embodiment of the present invention may include the first sheet substrate composed of nonwoven fabric or mesh sheet. The first sheet substrate composed of nonwoven fabric or mesh sheet has the advantage that such material increases the amount of the Cry polyhedron retained per unit area of the first sheet substrate. In addition, the porous structure of nonwoven fabric or mesh sheet enables easy manufacture of a floatable body by filling the first sheet substrate with bubbles.

The first sheet substrate may be a flat plate including plates, thin plates, sheets and films. One side or both sides of the flat plate may be smooth, or may be wholly or partially rough.

An insect control sheet according to another preferred embodiment of the present invention has a floating member for floating the insect control sheet on water which is bubbles or air cells contained in one of members comprising the insect control sheet.

In other words, the insect control sheet may include the first sheet substrate containing bubbles, a sheet-shaped second sheet substrate containing bubbles and layered on the top side of the first sheet substrate, and the toxin-containing matrix layer containing bubbles. In addition the first sheet substrate may be composed of two layers between which air cell is formed.

An insect control sheet according to yet another preferred embodiment of the present invention has a floating member for floating the insect control sheet on water which is a hydrophobic region formed on the surface of the insect control sheet.

In other words, the insect control sheet may include a patterned hydrophobic region formed on the underside of the first sheet substrate and the pure matrix layer and the toxin-containing matrix layer layered on the part of the underside of the first sheet substrate where the hydrophobic region is not formed. The insect control sheet may also include the hydrophobic region formed on the top side of the first sheet substrate.

Another insect control sheet according to a preferred embodiment of the present invention may include a design made on the underside of the first sheet substrate.

The design is made by printing or drawing, and the examples of the design are letters and graphics. The design may represent, for example, a sign indicating the time for the replacement of the insect control sheet or a caution for proper hygiene For example, the hydrophobic part patterned on the underside of the first sheet substrate mentioned above may be formed into a design including letters and graphics. The hydrophobic part may also be formed into a part of such letters and graphics. In addition, the design on the underside of the first sheet substrate may be covered with the pure matrix layer and the toxin-containing matrix layer to be hidden before the insect control sheet is used, and may appear after the use of the insect control sheet for a certain period as the result of the disappearance caused by the decomposition or the dissolution of the toxin-containing matrix layer and the pure matrix layer.

The method of exposing the design after the use of the insect control sheet for a certain period may include the use of the second and third materials colored with dyes. Edible dyes are preferable for coloring the insect control sheet used in a water tank of daily life water including drinking water.

An insect control article being used by floating on water according to another embodiment of the present invention comprises a body floatable on water,
a pure matrix layer layered on the underside of the body, and
a toxin-containing matrix layer layered on the underside of the pure matrix layer.
The insect control article also comprises:
the pure matrix layer comprises a degradable or water-soluble second material;
the toxin-containing matrix layer comprises a degradable or water-soluble third material and the Cry polyhedron; and
the toxin-containing matrix layer sustainably releases the Cry polyhedron to the water on which the insect control article is floated.

A transfer sheet according to another embodiment of the present invention is used to fabricate the insect control sheet or insect control article. The transfer sheet comprises the toxin-containing matrix layer containing the Cry polyhedron, the pure matrix layer, and an adhesive layer layered in the order on one surface of a transfer-sheet substrate. Also, the transfer sheet comprises;
the toxin-containing matrix layer comprising a degradable or water-soluble third material and the Cry polyhedron; and
the pure matrix layer comprising a degradable or water-soluble second material.

The present invention, preferred embodiments of the present invention and the elements contained therein can be combined as far as possible to work the invention.

Advantageous Effects of Invention

The insect control sheet according to one embodiment of the present invention includes the toxin-containing matrix layer composed of the degradable or water-soluble third material and the Cry polyhedron and the pure matrix layer sandwiched between the first sheet substrate and the toxin-containing matrix layer, in addition to other elements.

Owing to the structure, the Cry polyhedron is gradually released into water connected with the degradation or dissolution of the toxin-containing matrix layer. In addition, the pure matrix layer prevents the Cry polyhedron from contacting with the first sheet substrate so as to facilitate release of the Cry polyhedron.

The insect control article according to another embodiment of the present invention includes the toxin-containing matrix layer composed of the degradable or water-soluble third material and the Cry polyhedron, and the pure matrix layer sandwiched between the underside of the body and the toxin-containing matrix layer, in addition to other elements.

Owing to the structure, the Cry polyhedron is gradually released into water connected with the degradation or dissolution of the toxin-containing matrix layer. In addition, the pure matrix sheet prevents the Cry polyhedron from contacting with the first sheet substrate so as to facilitate release of the Cry polyhedron.

The transfer sheet according to another embodiment of the present invention includes, in addition to other elements, the toxin-containing matrix layer containing the Cry polyhedron, the pure matrix layer, and the adhesive layer layered in this order on one surface of the transfer-sheet substrate. Thus the transfer sheet can be used to transfer the layers from the transfer-sheet substrate to the first sheet substrate or the body of any forms and properties, and advantageously used to fabricate an insect control sheet or article having the layers of properly controlled thickness and uniformity.

BRIEF DESCRIPTION OF DRAWINGS

FIG. 1 is a sectional view illustrating the first insect control sheet 1*a*.

FIG. 2 is a sectional view illustrating the second insect control sheet 1*b*.

FIG. 3 is a sectional view illustrating the third insect control sheet 1*c*.

FIG. 4 is a sectional view illustrating the fourth insect control sheet 1*d*.

FIG. 5 is a sectional view illustrating the fifth insect control sheet 1*e*.

FIG. 6 is a sectional view illustrating the sixth insect control sheet 1*f*.

FIG. 7 is a sectional view illustrating the seventh insect control sheet 1*g*.

FIG. 8 is a sectional view illustrating the insect control article.

FIG. 9 is a sectional view illustrating the transfer sheet for fabricating the insect control article.

FIG. 10 is a sectional view illustrating the eighth insect control sheet 1*h*.

FIG. 11 is a sectional view illustrating the ninth insect control sheet 1*i*.

DESCRIPTION OF EMBODIMENT

The insect control sheet, insect control article, and transfer sheet according to the embodiments of the present invention are further described below referring to the figures. Some of the figures referred herein are schematic diagrams containing magnification of some elements for easy understanding of the present invention. Thus some of the dimensions or dimensional ratio between the elements may be different from that of the actual sheets and articles.

In the sectional views showing the layer structure, the blank between the layers is made for the convenience of explanation of the layer structure. In the actual insect control sheets or insect control articles, the layers are attached to each other.

The dimensions, materials, forms, and relative positions of the members and parts described in the working examples of the present invention merely explain the present invention and are not intended to restrict the scope of the present invention unless otherwise specified.

FIG. 1 is a sectional view illustrating the first insect control sheet 1*a*.

The first insect control sheet 1*a* includes the pure matrix layer 20 layered on the underside of the first sheet substrate 10 and the toxin-containing matrix layer 30 layered on the underside of the pure matrix layer 20.

In the present invention and in this specification, the top side and underside are defined for the explanation. When the insect control sheet is placed on water, the side contacting with water or sinking into water is defined as the underside while the side facing the atmosphere is defined as the top side. This applies to the insect control sheets from the second to ninth and the insect control article explained below.

The first sheet substrate 10 is a support member for the pure matrix layer 20 and the toxin-containing matrix layer 30. The first sheet substrate 10 is composed of the first material. The first material may be degradable, water-soluble, persistent, or poorly water soluble. The first material should preferably be degradable or water-soluble in terms of the protection of natural environment. The first material should preferably have low human health risks, because the insect control sheet may be used to control harmful insects in a water tank reserving daily life water.

The first sheet substrate has a sheet shape extending two-dimensionally. The sheet shape extending two-dimensionally includes, for example, sheet, film and paper. The thickness of the first sheet substrate is not specifically restricted, and preferably ranges from 16 μm (micrometers) to 3 mm (millimeters). A thickness within the range gives sufficient strength to the first sheet substrate and enables the pure matrix layer 20 and the toxin-containing matrix layer 30 to be readily layered. In addition, the first sheet substrate having such thickness facilitates designing of the time required for the decomposition of degradable materials in natural environment.

The two-dimensional size of the first sheet substrate is not specifically restricted, and may be determined according to the area of water surface in a water tank to which the insect control sheet is placed.

The pure matrix layer 20 separates the toxin-containing matrix layer 30 and the first sheet substrate 10. If the Cry polyhedron contained in the toxin-containing matrix layer contacted with the first sheet substrate, the Cry polyhedron would adhere to the first sheet substrate and would not be easily released from the first insect control sheet.

For solving the trouble mentioned above, the insect control sheet includes the pure matrix layer 20 which separates the toxin-containing matrix layer 30 and the first sheet substrate 10 to secure the release of the Cry polyhedron.

The pure matrix layer 20 is composed of the degradable or water-soluble second material. The second material should preferably have low human health risks, because the insect control sheet may be used to control harmful insects in a water tank reserving daily life water. The thickness of the pure matrix layer is not specifically restricted, and can be optionally determined, preferably within the range from 5 nm (nanometers) to 50 μm (micrometers). A thickness within the range enables the separation of the toxin-containing matrix layer 30 and the first sheet substrate 10.

The pure matrix layer 20 can be formed by coating, printing or dipping.

The term "pure" of the pure matrix layer 20 means that the layer is free of toxins. With this concept, the matrix layer containing toxins is called "the toxin-containing matrix layer 30". The material constituting the pure matrix layer 20 does not mean "a pure material purified by removing impurities to the utmost limit".

The toxin-containing matrix layer 30 is composed of the degradable or water-soluble third material and the Cry polyhedron. The toxin-containing matrix layer 30 releases the Cry polyhedron caused by the decomposition or dissolution of the third material.

The toxin-containing matrix layer 30 is composed of the degradable or water-soluble third material. The third material should preferably have low human health risks, because the insect control sheet may be used to control harmful insects in a water tank reserving daily life water. The thickness of the toxin-containing matrix layer 30 is not specifically restricted, and may be optionally determined preferably within the range from 5 nm (nanometers) to 1 mm (millimeter). A thickness within the range enables the release of the Cry polyhedron. The lower limit of the thickness, 5 nm (nanometers), is the thickness of the part of the toxin-containing matrix layer where only the third material constitutes the matrix layer (the part where the Cry polyhedron is not contained).

The Cry polyhedron is produced by fixing the Cry toxin to a polyhedron of polyhedrin protein, which is a protein microcrystal produced by Bombyxmori cypovirus (Bm-CPV). A tag for fixing the Cry toxin to the polyhedron of polyhedrin protein is added to the N-terminal of the Cry toxin. Then the tagged Cry toxin is fixed to the polyhedron of polyhedrin protein. In the method, the Cry toxin can be fixed to the polyhedron by adding the N-terminal α-helix H1 (refer to Reference C-1) of the polyhedrin protein to the N terminal of the Cry toxin. The polyhedron, which solubilizes at a pH of 10 or more, functions as a carrier suitable for the Cry toxin, because the polyhedron solubilizes under the alkaline condition in the digestive tract of mosquito larvae (refer to Reference C-2). The diameter of the circumscribed sphere of the Cry polyhedron, which represents the size of the Cry polyhedron, ranges from 3 μm (micrometers) to 15 μm (micrometers).

The Cry toxin fixed to the Cry polyhedron and contained in the toxin-containing matrix layer is an insecticidal protein usually produced by bacteria included in *Bacillus thuringiensis* and its varieties or subspecies. Preferable Cry toxins are Cry11Aa, Cry4Aa, Cry4Ba, and Cry10Aa produced by *Bacillus thuringiensis* serovar israelensis, and Cry11Aa is more preferable.

Cry11Aa is highly toxic to the larvae of Aedes which transmit arbovirus including dengue virus, Culex which transmit filaria, and Anopheles which transmit plasmodium (refer to Reference C-3).

Reference

Reference C-1: Hiroshi Ijiri, Fasseli Coulibaly, Gento Nishimura et al., Structure-based targeting of bioactive proteins into cypovirus polyhedra and application to immobilized cytokines for mammalian cell culture, Biomaterials 30 (2009) 4297-4308

Reference C-2: Despres Laurence, Lagneau Christophe & Frutos Roger, Using the Bio-Insecticide *Bacillus thuringiensis* israelensis in Mosquito Control, Pesticides in the Modern World—Pests Control and Pesticides Exposure and Toxicity Assessment, Edited by Dr. Margarita Stoytcheva, Publisher In tech, September, 2011

Reference C-3: Jesko Oestergaad, Ralf-Udo Ehlers, Amparo C. Martinerz-Ramirez et al., Binding of Cyt1Aa and Cry11Aa Toxins of *Bacillus thuringiensis* Serovar israelensis to Brush Border Membrane Vesicles of Tipula paludosa (Diptera: Nematocera) and Subsequent Pore Formation, Applied and Environmental Microbiology, Vol. 73, No. 11, (June 2007) 3623-3629

The toxin-containing matrix layer 30 can be formed by coating or printing with a mixture prepared by mixing the third material and the Cry polyhedron.

The first insect control sheet 1a floats on water, and sustainably releases the Cry polyhedron into the habitat of mosquito larvae between water surface and several centimeters below water surface to make mosquito larvae ingest the Cry polyhedron.

The Cry polyhedron is sustainably released into water from the toxin-containing matrix layer 30 when the first insect-control sheet 1a is placed on water surface.

The first material is a constituent of the first sheet substrate 10. Examples of the degradable or water-soluble first material include starches and starch mixtures with polylactic acid, chitin, chitosan, polyhydroxyalkanoates, polybutylene succinate, cellulose and protein; and natural fibers (cotton, wool, hemp, pulp, silk, kenaf, banana fiber and bamboo fiber) and their blends. These examples have low human health risks.

Examples of the persistent first material include resin sheets of polypropylene resins, polyethylene resins, polyamide resins, polyester resins, acrylic resins, polyvinyl chloride resins, polycarbonate resins, polyurethane resins, polystyrene resins, and acetate resins; cellulose sheets, such as glassine paper, coated paper, and cellophane; and composites of those materials.

The third material is a matrix material constituting the toxin-containing matrix layer 30. Examples of the third material include collagen, gelatin, chitin, chitosan, glycosaminoglycan, hyaluronic acid, chondroitin sulfate, elastin, fibronectin, laminin, fibrin, alginic acid, fibroin, starch, pectin, pectic acid, agarose, heparin, carboxymethyl cellulose, cellouronic acid, polyvinyl alcohol, polyethylene glycol, methyl polymethacrylate, methacrylate ester polymers, silicone resins, polylactic acid, polyglycolic acid, polyε-caprolactone, bovine serum albumin, casein, sucrose, and the mixtures, polymers, copolymers and cross-linked products of those substances. These examples have low human health risks.

The second material is a constituent of the pure matrix layer 20. Examples of the second material are the same as that mentioned in the description of the third material.

The second and third materials for the first insect control sheet 1a should preferably consist of the same ingredients, because the degradation time of the toxin-containing matrix layer 30 and the pure matrix layer 20 can be easily designed in designing the first insect control sheet 1a. In addition, the first insect control sheet 1a can be produced with a smaller number of materials and in a simpler process which enable easier process control.

The sheet substrate 10 of the first insect control sheet 1a should preferably be composed of the degradable first material, and the second and third materials should preferably degrade or dissolve in water faster than the first material, because the second and third materials having such properties ensure that all of the Cry polyhedron contained in the toxin-containing matrix layer 30 will be gradually released.

The time required for the toxin-containing matrix layer 30 to degrade or dissolve in water should range usually from 15 days to 90 days, preferably from 15 days to 60 days, and more preferably from 25 days to 45 days.

The time required for the pure matrix layer 20 to degrade or dissolve in water should range usually from the time 5 days shorter to the time 10 days longer than the time required for the degradation or dissolution of the toxin-containing matrix layer, preferably from the time 3 days shorter to the time 10 days longer, and more preferably from the time 1 day shorter to the time 1 day longer. The time required for the degradation or dissolution of the layers, however, cannot usually be designed by the day (24 hours), because the advancement of the degradation or dissolution of the layers is influenced by water temperature and quality which vary greatly. The degradation time is therefore forced to be set up roughly on a monthly basis. It is preferable to design the time required for the degradation or dissolution of the two layers by employing the same material for the second and third materials to synchronize their degradation and controlling the thickness of the layers and concentration of the materials in the layers.

The degradable or water-soluble first sheet substrate usually degrades or dissolves in water in 180 days and should preferably degrade or dissolves in the time from 30 days to 60 days longer than the time required for the toxin-containing matrix layer to degrade or dissolve in water.

The first sheet substrate may be composed of nonwoven fabric or mesh sheet.

The eighth insect control sheet 1*h* schematically drawn in FIG. 10 is composed of the first sheet substrate 10 of nonwoven fabric. The surface of the nonwoven fabric is designed to form convexes and concaves which are larger than the Cry polyhedron 51. Thus the insect control sheet composed of the first sheet substrate of nonwoven fabric retains greater amount of the Cry polyhedron per unit area than the insect control sheet composed of the first sheet substrate of a flat plate. In addition, the porous structure of nonwoven fabric facilitates the manufacture of floatable object where the first sheet substrate is aerated.

The diagram of the eighth insect control sheet 1*h* in FIG. 10 shows the first sheet substrate 10, the pure matrix layer 20, and the toxin-containing matrix layer 30 being attached to each other without having a space between them.

The first material constituting the nonwoven fabric of the first sheet substrate 10 may be selected from various materials without any restriction. Natural fibers (cotton, wool, hemp, pulp, silk, kenaf, banana fiber, and bamboo fiber, etc.) are preferable for the first material because of their low human health risks.

The ninth insect control sheet 1*i* schematically drawn in FIG. 11 is composed of the first sheet substrate 10 of mesh sheet. The surface of the mesh sheet is designed to form convexes and concaves which are larger than the Cry polyhedron 51. Thus the insect control sheet composed of the first sheet substrate of mesh sheet retains greater amount of the Cry polyhedron per unit area than the insect control sheet composed of the first sheet substrate of a flat plate. In addition, porous structure of mesh sheet facilitates the manufacture of floatable object where the first sheet substrate is aerated.

The diagram of the ninth insect control sheet 1*i* in FIG. 11 shows the first sheet substrate 10, the pure matrix layer 20, and the toxin-containing matrix layer 30 being attached to each other without having a space between them.

FIG. 2 is a sectional view illustrating the second insect control sheet 1*b*. The second insect control sheet 1*b* is different from the first insect control sheet 1*a* in the property that the second insect control sheet 1*b* includes the first sheet substrate containing bubbles. Other properties such as the elements and the materials constituting the layers are the same as that of the first insect control sheet 1*a*. The first sheet substrate, which makes the difference, is explained below.

The second insect control sheet 1*b* includes the bubble-containing first sheet substrate 10*a*. The bubble-containing first sheet substrate 10*a* contains a plurality of bubbles 16. Thus the bubble-containing first sheet substrate 10*a* has low specific gravity and decreases the specific gravity of the second insect control sheet 1*b* to make the sheet floatable on water.

The bubble-containing first sheet substrate 10*a* is manufactured in the processes as exemplified below:

(1) Forming the first material into a sheet, holding the first material sheet in a pressurized inert atmosphere to make the sheet contain the inert gas, and foaming the first material sheet by heating under normal pressure;

(2) Forming the first material into a sheet, simultaneously making the sheet contain water, and foaming the water-containing sheet by heating; or (3) Making a bubble-containing material by adding a known blowing agent including hydrocarbons such as propane or ethers such as dimethyl ether to the first material.

FIG. 3 is a sectional view illustrating the third insect control sheet 1*c*. The third insect control sheet 1*c* is different from the first insect control sheet 1*a* in the property that the third insect control sheet includes the bubble-containing second sheet substrate 11 layered on the first sheet substrate 10. Other properties such as the elements and the materials constituting the layers are the same as that of the first insect control sheet 1*a*. The bubble-containing second sheet substrate, which makes the difference, is explained below.

The third insect control sheet 1*c* includes the bubble-containing second sheet substrate 11 layered on the top side of the first sheet substrate 10. The bubble-containing second sheet substrate 11 contains a plurality of bubbles 16. The bubble-containing second sheet substrate 11 has low specific gravity and decreases the specific gravity of the third insect control sheet 1*c* to make the sheet floatable on water.

The third insect control sheet 1*c* is manufactured by, for example, forming the pure matrix layer 20 and the toxin-containing matrix layer 30 on the first sheet substrate 10 and layering or bonding the bubble-containing second sheet substrate 11 on the top side of the first sheet substrate 10.

The materials, foaming process, and degradation or dissolution time of the bubble-containing second sheet substrate 11 are the same as that of the first sheet substrate 10. The foaming process for the bubble-containing second sheet substrate 11 is the same as that for foaming the bubble-containing first sheet substrate 10*a*.

FIG. 4 is a sectional view illustrating the fourth insect control sheet 1*d*. The fourth insect control sheet 1*d* is different from the first insect control sheet 1*a* in the property that the fourth insect control sheet 1*d* includes the toxin-containing matrix layer containing bubbles. Other properties such as the elements and the materials constituting the layers are the same as that of the first insect control sheet 1*a*. The bubble-toxin-containing matrix layer 30*a*, which makes the difference, is mentioned below.

The bubble-toxin-containing matrix layer 30*a*, one of the elements of the fourth insect control sheet 1*d*, contains a plurality of bubbles 56 and the Cry polyhedron 51. The bubble-toxin-containing matrix layer 30*a* has low specific gravity and decreases the specific gravity of the fourth insect control sheet 1*d* to make the sheet floatable on water.

The bubble-toxin-containing matrix layer 30*a* is manufactured in the processes as exemplified below:

(1) Adding bubbles, such as air bubbles, to a mixture of the third material and the Cry polyhedron being knead, and hardening the mixture; and (2) Manufacturing a bubble-containing material by adding a known blowing agent including hydrocarbons such as propane or ethers such as dimethyl ether to a mixture of the third material and the Cry polyhedron.

FIG. 5 is a sectional view illustrating the fifth insect control sheet 1*e*.

The fifth insect control sheet 1*e* is different from the first insect control sheet 1*a* in the property that the fifth insect control sheet 1*e* includes the first sheet substrate having two layers between which air cells are contained. Other properties such as the elements and the materials constituting the layers are the same as that of the first insect control sheet 1*a*. The double-layered first sheet substrate, which makes the difference, is mentioned below.

The fifth insect control sheet 1e include the first sheet substrate 10 having two layers composed of the top first sheet substrate 10b and the bottom first sheet substrate 10c. The top first sheet substrate 10b and the bottom first sheet substrate 10c are partially separated to form air cells 15. Thus the first sheet substrate 10 composed of the top first sheet substrate 10b and the bottom first sheet substrate 10c has low specific gravity to decrease the specific gravity of the fifth insect control sheet 1e so as to make the sheet floatable on water.

Figure 5:
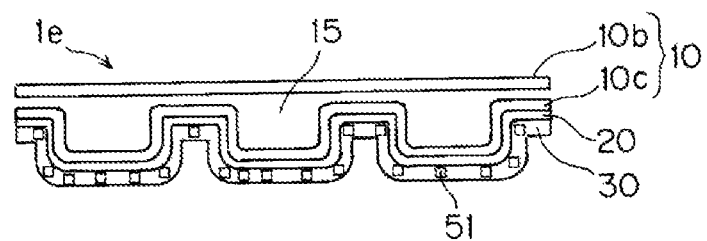

FIG. 5 shows the bottom sheet substrate 10c, the pure matrix layer 20, and the toxin-containing matrix layer 30 being attached to each other.

Figure 6:
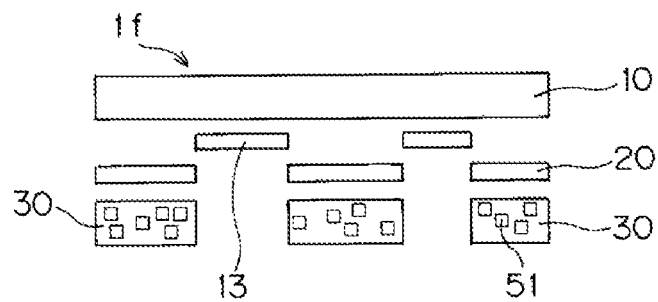

FIG. 6 is a sectional view illustrating the sixth insect control sheet 1f.

The sixth insect control sheet 1f includes the hydrophobic region 13 made into a pattern on the underside of the first sheet substrate 10, and also includes the pure matrix layer 20 and the toxin-containing matrix layer 30 layered on the underside of the first sheet substrate where the hydrophobic region is not made. The patterns of the hydrophobic region 13 include, for example, checkered patterns, latticed patterns and dot patterns. The relative position of the hydrophobic region and the layers including the pure matrix layer can be described as an alternate arrangement.

Substances, especially sheet-shaped substances, coated with a hydrophobic material is floatable on water. The sixth insect control sheet 1f has the hydrophobic regions on its underside which are formed partially and exposed. Thus the sixth insect control sheet 1f is floatable on water.

The hydrophobic region may be formed by spreading a hydrophobic material. The hydrophobic region may also be formed by applying a water-repellent finish on the surface of the first sheet substrate 10. Examples of the hydrophobic material include fluorochemical water-and-oil repellent agents and particulate hydrophobic oxides (refer to Reference C-4). Examples of the water-repellent finish include embossing.

Reference

Reference C-4: JP 4348401

Figure 7:
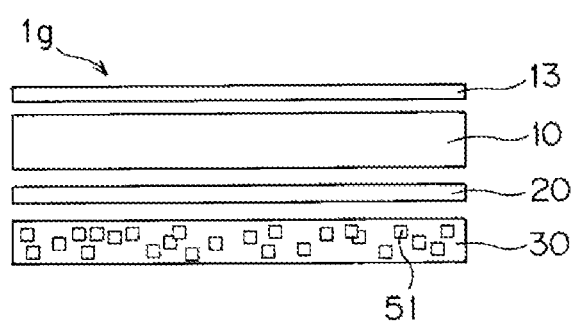
Figure 8:
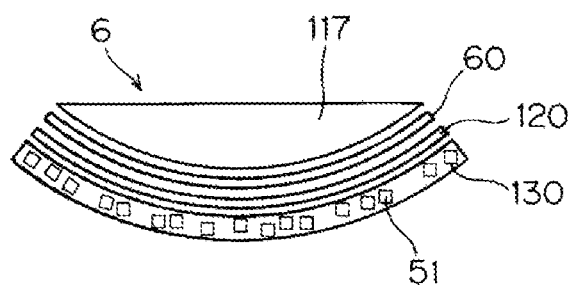

FIG. 7 is a sectional view illustrating the seventh insect control sheet 1g.

The seventh insect control sheet 1g includes the hydrophobic region formed on the first sheet substrate 10 in the same manner as that of the sixth insect control sheet 1f. The hydrophobic region 13 of the seventh insect control sheet 1g is formed on the top side of the first sheet substrate. Other properties such as the elements and the materials constituting the layers are the same as that of the first insect control sheet 1a.

As shown in FIG. 7, the hydrophobic region 13 of the seventh insect control sheet 1g is formed on the top side of the first sheet substrate 10. The hydrophobic region 13 is exposed on the outside of the seventh insect control sheet 1g to make the sheet floatable on water.

The hydrophobic region 13 may be formed all over the top side of the first sheet substrate 10 or on some part of the top side of the first sheet substrate 10. Making the hydrophobic region all over the top side is advantageous to easy forming of the hydrophobic region.

The design may be made on the underside of the first sheet substrate of any of the insect control sheets of the first to the ninth. The design includes letters and graphics, and may be made by printing, drawing, or embossing the surface of the first sheet substrate. Examples of the design include caution for the replacement of the insect control sheet, disposal methods for the first sheet substrate, and notice for proper hygiene.

At the beginning of the use of the insect control sheet, the underside of the first sheet substrate is covered with the pure matrix layer and toxin-containing matrix layer which make the design invisible. At the final term of the use, the pure matrix layer and toxin-containing matrix layer disappear to make the design visible and attract the attention of the user.

The design should preferably be printed or drawn with edible inks for the insect control sheet used in a water tank of daily life water including drinking water.

The pure matrix layer and/or the toxin-containing matrix layer may be colored to hide the design more effectively at the beginning of using the insect control sheet. The layers of the insect control sheet used in a water tank of daily life water including drinking water should preferably be colored with food dyes.

FIG. 8 is a sectional view illustrating the insect control article.

The insect control article 6 includes the pure matrix layer 120 layered on the underside, which contacts with water, of the body 117 floatable on water, and the toxin-containing matrix layer 130 containing the Cry polyhedron is layered on the underside of the pure matrix layer.

The pure matrix layer 120 is composed of the degradable or water-soluble second material, and the toxin-containing matrix layer 130 is composed of the degradable or water-soluble third material and the Cry polyhedron 51.

The materials and forms of the body 117 are not specifically restricted, and can be selected from any materials and forms which make the body floatable on water and capable of sustainably releasing the Cry polyhedron 51 from the toxin-containing matrix layer layered on the body 117. Examples of the forms and materials of the body 117 include wooden bodies of various forms and boat-shaped or lid-shaped bodies of metals or synthetic resins.

The pure matrix layer is layered on the underside of the body which contacts with water.

The surface of the body 117 and the pure matrix layer 120 are bonded by the adhesive layer 60. The materials of the adhesive layer include fibrin glue, gelatin glue, cyanoacrylates, urethane prepolymers, hydrogels, cross-linked polysaccharides, natural adhesive resins such as Japanese lacquer, mixtures of these materials, and mixtures of these materials and biodegradable resins. These materials mentioned here have low human health risks.

The structure of the toxin-containing matrix layer 130 is the same as that of the toxin-containing matrix layer 30 of the insect control sheets. The matrix material constituting the toxin-containing matrix layer 130 are the same as that of the third material for the insect-control sheets. The structure of the pure matrix layer 120 is the same as that of the pure matrix layer 20 of the insect control sheets. The material constituting the pure matrix layer 120 are the same as that of the second material for the insect-control sheets.

FIG. 9 is a sectional view illustrating the transfer sheet for fabricating the insect control article.

The transfer sheet 70 is fabricated by layering the toxin-containing matrix layer 130, the pure matrix layer 120 and the adhesive layer 60 in the order on one surface of the transfer-sheet substrate 71. The materials of the layers are the same as those mentioned in the description of the insect control article 6.

Examples of the transfer-sheet substrate 71 include a sheet of polyvinyl alcohol (PVA). The insect control article 6 can be fabricated by floating the transfer sheet 70 on water surface and pressing the body 117 against the transfer sheet to transfer the layers from the sheet to the body. The PVA dissolves in water to disappear.

The transfer sheet 70 is capable of forming insect control layers on the body 117 having a curved surface.

Figure 9:
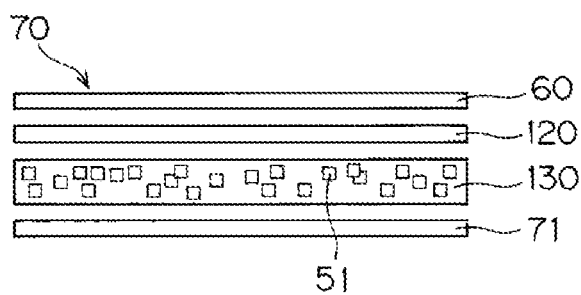
Figure 10:
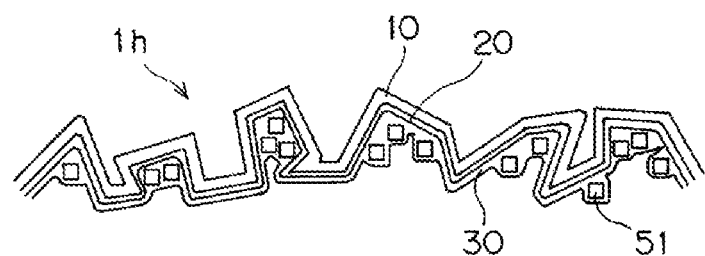
Figure 11:
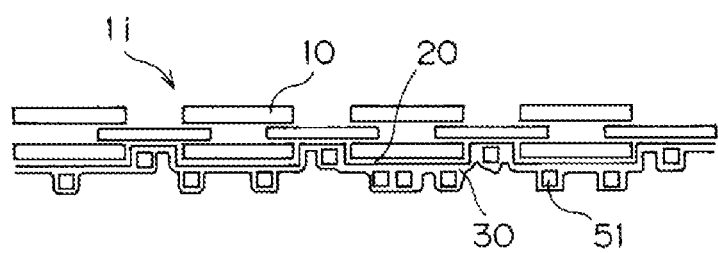

The transfer sheet 70 mentioned by reference to FIG. 9 is a so-called water transfer sheet. The transfer sheet for fabricating the insect control article may be a transfer sheet ordinary used for transfer printing in the air. A film finished with a release agent may be employed for the substrate of such transfer sheets.

Examples of materials used for the transfer-sheet substrate include sheets of resins such as polypropylene resins, polyethylene resins, polyamide resins, polyester resins, acrylic resins, polyvinyl chloride resins, polycarbonate resins, polyurethane resins, polystyrene resins and acetate resins; cellulose sheets such as glassine paper, coated paper, and cellophane; and sheets of the composite of these materials.

The transfer sheet 70 may be used to fabricate the insect control sheets.

The insect control sheets and articles mentioned above may include the toxin-containing layer and/or the pure matrix layer containing feeds liked by harmful insects, such as yeast. Such layers attract harmful insects near the insect control sheets and articles to improve the effect of insect control.

REFERENCE SIGNS LIST

1a: First insect control sheet
1b: Second insect control sheet
1c: Third insect control sheet
1d: Fourth insect control sheet
1e: Fifth insect control sheet
1f: Sixth insect control sheet
1g: Seventh insect control sheet
1h: Eighth insect control sheet
1i: Ninth insect control sheet
6: Insect control article
10: First sheet substrate
10a: Bubble-containing first sheet substrate
10b: Top first sheet substrate
10c: Bottom first sheet substrate
11: Bubble-containing second sheet substrate
12: Hydrophobic part
13: Hydrophobic part
15: Air cell
16: Bubble
20: Pure matrix layer
30: Toxin-containing matrix layer
30a: Bubble-toxin-containing matrix layer
51: Cry polyhedron
56: Bubble
60: Adhesive layer
70: Transfer sheet
71: Transfer-sheet substrate
117: Body
120: Pure matrix layer
130: Toxin-containing matrix layer

The invention claimed is:

1. An insect control sheet for floating on water, comprising:
a sheet-shaped first sheet substrate comprising a degradable first material,
a pure matrix layer layered on an underside of the first sheet substrate;
a toxin-containing matrix layer layered on an underside of the pure matrix layer;
a floating member for floating the insect control sheet on water contained in one of the first substrate, the pure matrix layer and the toxin-containing matrix layer,
wherein the pure matrix layer comprises a degradable or water-soluble second material,
the toxin-containing matrix layer comprises a degradable or water-soluble third material and Cry polyhedron that is an insecticidal protein produced by *Bacillus thuringiensis* fixed to a polyhedron of polyhedrin protein,
the toxin-containing matrix layer is adapted to release the Cry polyhedron by decomposition or dissolution of the third material, to the water on which the insect control sheet floats, and
the toxin-containing matrix layer and the pure matrix layer degrade or dissolve in water in a shorter time than that required for the decomposition or dissolution of the first sheet substrate.

2. The insect control sheet according to claim 1, wherein the second material is composed of same ingredients as that of the third material.

3. The insect control sheet according to claim 1, wherein the third material comprises at least one ingredient selected from the group consisting of collagen, gelatin, chitin, chitosan, glycosaminoglycan, hyaluronic acid, chondroitin sulfate, elastin, fibronectin, laminin, fibrin, alginic acid, fibroin, starch, pectin, pectic acid, agarose, heparin, carboxymethyl cellulose, cellouronic acid, polyvinyl alcohol, polyethylene glycol, methyl polymethacrylate, methacrylate ester polymers, silicone resins, polylactic acid, polyglycolic acid, polyε-caprolactone, bovine serum albumin, casein, sucrose, and mixtures, polymers, copolymers and cross-linked products thereof.

4. The insect control sheet according to claim 1, wherein the first sheet substrate comprises nonwoven fabric or mesh sheet.

5. The insect control sheet according to claim 1, wherein the floating member comprises bubbles contained in the first sheet substrate.

6. The insect control sheet according to claim 1, further comprising a sheet-shaped second sheet substrate that is layered on a top side of the first sheet substrate,
wherein the floating member comprises bubbles contained in the second sheet substrate.

7. The insect control sheet according to claim 1, wherein the floating member comprises bubbles contained in the toxin-containing matrix layer.

8. The insect control sheet according to claim 1, wherein the first sheet substrate comprises two layers, and the floating member comprises an air cell being formed between the two layers of the first sheet substrate.

9. The insect control sheet according to claim 1, wherein the floating member comprises a patterned hydrophobic region being formed on the underside of the first sheet substrate, and the pure matrix layer and toxin-containing matrix layer are layered on a part of the underside of the first sheet substrate where the hydrophobic region is not formed.

10. The insect control sheet according to claim 1, wherein the floating member comprises a hydrophobic region being formed on a top side of the first sheet substrate.

11. The insect control sheet according to claim 1, wherein a design is made on the underside of the first sheet substrate.

* * * * *